Figures 1, 2:
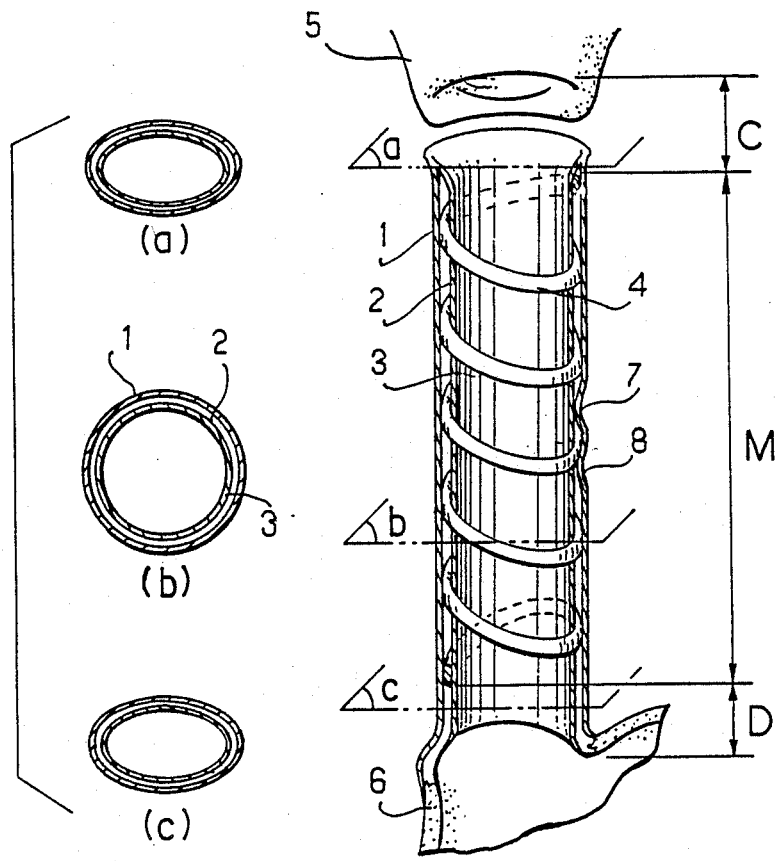

United States Patent [19]

Galtier

[11] Patent Number: 4,747,849

[45] Date of Patent: May 31, 1988

[54] OESOPHAGUS PROSTHESIS

[76] Inventor: Claude Galtier, 13, Avenue Maillol, 95370 Montigny Les Cormeilles, France

[21] Appl. No.: 2,859

[22] Filed: Jan. 13, 1987

[30] Foreign Application Priority Data

Jan. 13, 1986 [FR] France ............................ 86 00464

[51] Int. Cl.$^4$ ............................................. A61F 2/04
[52] U.S. Cl. .................................................... 623/12
[58] Field of Search ............... 623/12, 10, 1; 128/1 R, 128/334 R

[56] References Cited

U.S. PATENT DOCUMENTS

| | | | |
|---|---|---|---|
| 3,105,492 | 10/1963 | Jeckel | 623/1 X |
| 3,479,670 | 11/1969 | Medell | 623/1 |
| 4,086,665 | 5/1978 | Poirier | 623/1 |
| 4,130,904 | 12/1978 | Whalen | 623/1 |
| 4,403,604 | 9/1983 | Wilkinson et al. | 623/12 X |

FOREIGN PATENT DOCUMENTS

| | | | |
|---|---|---|---|
| 2513111 | 3/1983 | France | 623/12 |
| 2069339 | 8/1981 | United Kingdom | 623/12 |
| 137632 | 1/1961 | U.S.S.R. | 623/12 |
| 214017 | 3/1968 | U.S.S.R. | 623/12 |

OTHER PUBLICATIONS

"Plastic Tube Substituted for Esophagus", *Braces Today*, Newsletter of the Pope Foundation, Inc., 197 South West Ave., Kankakee, Ill., Nov. 1952 (2 pages).
Medical & Biological Engineerign & Computing, vol. 23, No. 1, janvier 1985, pp. 77-78, Londres, GB; D. P. Orr et al.

*Primary Examiner*—Ronald L. Frinks
*Attorney, Agent, or Firm*—Frishauf, Holtz, Goodman & Woodward

[57] ABSTRACT

Implantable prosthesis fulfilling the natural functions of the oesophagus, characterized in that it consists of a double-walled tube of circular cross-section in its midportion and of elliptical cross-section towards its extremities, the exterior wall being made of a relatively rigid hemocompatible synthetic material and the interior wall being made of a flexible hemocompatible synthetic material providing a perfectly smooth internal surface, a helicoidal band of relatively elastic material being inserted between the two walls in the midportion of said tube.

4 Claims, 1 Drawing Sheet

OESOPHAGUS PROSTHESIS

The present invention concerns a new prosthesis usable to replace the oesophagus and is implantable in any patient afflicted by disease or impairment of this organ.

Statistics reveal that the number of such patients increases steadily in the world and that origins of these impairments can be very diverse:
- congenital defects
- impairments due to ingestion of "corrosive products"
- impairments of traumatic origin
- diverse and ulcerous diseases
- diseases due to malignant tumors.

Very few treatments of these impairments are possible, but in any event, there has not existed up to now any prosthesis permitting:
- Prolongation of the life of the patient for more than two years
- Avoidance of the recurrence of a tumor
- Assuring, within the time limits of a surgical operation, and intervention permitting putting in place an implant re-establishing the hyper-pharyngo-gastric continuity.

The present invention eliminates all these difficulties by way of a prosthesis of completely new conception which is simple in construction and simple to implant and fulfills the natural functions of the oesophagus by transmission of the aortic, bronchial and diaphragmic peristalses and permitting the definitive erradication of the initial pathology for which the intervention is performed within a period suitable for surgery.

This prothesis consists of a double-walled tube, of circular cross-section in its midportion and of eliptic cross-section towards its extremities, the exterior wall being made of a hemocompatible relatively rigid synthetic material and the interior wall being made of a flexible hemocompatible synthetic material having a perfectly smooth internal surface, a helicoidal band of relatively elastic material being inserted between the two walls in the midportion of the said tube.

In the practice of the invention, the synthetic material will preferably be a polyurethane in which rigidity and flexibility depend upon the degree of cross-linking and on the nature and proportional content of the plasticizer, the various qualities of this materials and their physical and mechanical properties being well known.

For illustration of the invention, the annexed drawing represents:

FIG. 1, the artificial oesophagus according to the invention, in vertical section, and FIGS. 2a, 2b and 2c, horizontal sections at various levels of the prosthesis of FIG. 1.

In the drawing, there has been designated by reference numeral 1 the exterior wall of the prosthesis and by reference numeral 2, the interior wall. The material of the wall 1 is relatively rigid, even though sufficiently supple to react to the peristalsis of the environing organs. The wall may have a thickness from 0.3 to 0.5 mm.

Made of the same material, the wall 2 must be sufficiently flexible to react to the deformations provoked by the wall 1 in such a way as to produce the transfer of an alimentary swallow. This wall 2 will similarly have a thickness of the order of 0.5 to 0.8 mm.

In the space 3 located between the two walls, of a breadth of the order of 3 mm, a helicoidal band 4 of flexible and elastic material is located. The function of this band is to transmit elastically to the interior wall 2 the deformations undergone by the exterior wall 1.

The midportion M of the tube is about 18–20 cm in length and, as shown by FIG. 2b, is of circular cross-section. The end portions, constituing the cervical oesophagus C (about 5 cm long) and the subdiaphragmic oesophagus (about 3 cm long), are of elliptical cross-section and as FIGS. 2a and 2c respectively show. It is these funnel-shaped sections which are intended to be connected respectively to the cricoid cartilage 5 and to the stomach 6 in a manner that is tight against leakage through these joints.

The functioning of this prosthesis is based on the anatomic contractions and the pressure exercised at these levels by the following organs in succession:
- the ring of Killian at the level of the upper funnel C
- the aortic contraction 7
- the bronchial contraction 8 (produced by the left bronchial tube)
- and the diaphragm contraction, at the level of the lower funnel D When an alimentary bolus (swallow of food) passes through the cricoid sphincter 5, the latter dilates the upper part C of the oesophagus and then the bolus is ejected into the midportion M, which contains the spring 4.

This spring transmits to the interior wall 2 the sequential pressues exerted on the exterior wall 1 by the aorta in the zone 7 and then by the bronchial tube in the zone 8. The bolus thus progresses by the effect of this peristalsis in a few seconds down to the portion D of the oesophagus and is ejected into the stomach, the smooth surface of the internal wall 2 assuring its total evacuation.

It will be noted that in addition to the stablity of the prosthesis as a whole, the relative rigidity of the wall 1 prevents the crushing of the tube on itself when the patient is in a stretched out position.

The implantation of this prosthesis is performed with the usual surgical techniques and raises no particular problems. On the contrary, the double wall of the tube facilitates a perfectly tight anastomosis, for example by means of a nonreabsorbable suture of the monofilament type, all risk of a fistula at the levels of the suture points being avoided by providing terminal adhesion.

The prosthesis according to the invention thus constitutes a most reliable solution for the diverse afflictions or impairments of the oesophagus, for which the existing treatments could hardly leave any hope of survival for more than two years. This technique, moreover, eliminates the risks of relapse, since in the majority of cases, cancers of the oesophagus are practically always primitive.

FIG. 1 shows indentations of the outer tube 1 at 7 and 8 respectively produced by pressure of the aorta and of the left bronchial tube when the oesophagus prosthesis is in place in the patient's body. The space between the outer tube 1 and the inner tube 2, maintained by the elastic helically wound band 4, prevents or reduces deformation of the inner tube 2 by deformations produced in the relatively more rigid tube 1 by the aorta and by the left bronchial tube.

Although the lower end of the prosthesis is shown joined to the patient's stomach 6, the upper end is shown spaced apart from the cricoid cartilage 5 in order to show better the preferred shape of the elliptical mouth of the tube, which is seen somewhat in perspective as well as partly in section, as indicated in the drawing by the section planes a, b and c respectively relating to FIGS. 2a, 2b and 2c.

Although up to now polyurethane plastics of the desired qualities of rigidity, flexibility and elasticity are preferred not only for the more rigid outer tube 1 and the more supple or flexible inner tube 3, but also for the elastic helical/piece 4 other synthetic materials compatible with blood and live tissue may be used, such as polytetrafluoroethylene (PTFE, "Teflon") or silicone polymers.

The helical piece 4 may conveniently be either of round or quadrangular cross-section.

The elliptical orifices of the prosthesis are, as shown, both elongated in substantially the same plane, and are both in planes substantially parallel to the axis of the cylindrical midportion of the device. It is of course possible to provide carefully devised asymmetries in these shape factors on the basis of anatomical geometry, although the illustrated essentially symmetrical device has been found to be quite satisfactory in this regard in practice up to now.

Thus, it will be understood that although the invention has been described with reference to a particular illustrative example, variations and modifications are possible within the inventive concept.

I claim:

1. Implantable prosthesis fulfilling the natural functions of the oesophagus, characterized in that it consists of a double-walled tube of circular cross-section in its midportion and of elliptical cross-section towards its extremities, comprising an exterior wall made of a relatively rigid hemocompatible synthetic material and an interior wall made of a flexible hemocompatible synthetic material providing of perfectly smooth internal surface, a helicoidal band of relatively elastic material being inserted between the two walls in the midportion of said tube.

2. Prosthesis according to claim 1 characterized in that said synthetic material is a polyurethane.

3. Prosthesis according to claim 1, wherein the end portions of the inner and outer tubes provide funnel-like transitions between the cylindrical shape of the middle portions of the respective tubes and an elongated substantially elliptical orifice for the prosthesis of a shape suitable for fluid-tight surgical attachment of living tissue.

4. Prosthesis according to claim 3, wherein said elliptical orifices of the respective end portions of the prosthesis are elongated in substantially the same plane.

* * * * *